US012672919B2

(12) United States Patent
You et al.

(10) Patent No.: US 12,672,919 B2
(45) Date of Patent: Jul. 7, 2026

(54) METHOD FOR OPERATING A ROBOTIC VISUALIZATION SYSTEM, AND ROBOTIC VISUALIZATION SYSTEM

(71) Applicant: Carl Zeiss Meditec AG, Jena (DE)

(72) Inventors: Fang You, Aalen (DE); David Dobbelstein, Ulm (DE); Joachim Steffen, Westhausen (DE)

(73) Assignee: Carl Zeiss Meditec AG, Jena (DE)

( * ) Notice: Subject to any disclaimer, the term of this patent is extended or adjusted under 35 U.S.C. 154(b) by 500 days.

(21) Appl. No.: 18/121,183

(22) Filed: Mar. 14, 2023

(65) Prior Publication Data

US 2023/0310089 A1     Oct. 5, 2023

(51) Int. Cl.
*A61B 34/20*         (2016.01)
*A61B 34/30*         (2016.01)

(52) U.S. Cl.
CPC .............. *A61B 34/20* (2016.02); *A61B 34/30* (2016.02); *A61B 2034/2055* (2016.02)

(58) Field of Classification Search
CPC .. A61B 34/20; A61B 34/30; A61B 2034/2055
See application file for complete search history.

(56) References Cited

U.S. PATENT DOCUMENTS

| | | | |
|---|---|---|---|
| 2020/0008874 A1* | 1/2020 | Barbagli | G16H 20/40 |
| 2022/0135346 A1* | 5/2022 | Matsuoka | B65G 47/917 |
| | | | 700/245 |
| 2022/0160445 A1* | 5/2022 | Meglan | B25J 9/1676 |
| 2022/0288781 A1* | 9/2022 | Schoessler | B25J 9/1651 |
| 2023/0190394 A1* | 6/2023 | Tam | A61B 34/37 |
| | | | 606/1 |
| 2023/0293249 A1* | 9/2023 | Yokoyama | B25J 13/00 |
| | | | 606/130 |
| 2023/0293258 A1* | 9/2023 | Nishimura | A61B 90/361 |
| | | | 600/160 |

FOREIGN PATENT DOCUMENTS

WO     WO-2020/190832 A1     9/2020

OTHER PUBLICATIONS

German Office Action for German Application No. 10 2022 107 818.3, mailed Dec. 13, 2022 (20 pages).

* cited by examiner

*Primary Examiner* — Jay Khandpur
(74) *Attorney, Agent, or Firm* — NIXON PEABODY LLP; Jeffrey L. Costellia

(57)         ABSTRACT

A method and associated system for operating a robotic visualization system comprising an imaging optical unit and a robotic arm for positioning the imaging optical unit within a surround. The method includes ascertaining a target field of view to be visualized by means of the imaging optical unit. Ascertaining a target pose of the robotic visualization system for capturing an image of the target field of view with a first imaging configuration of the imaging optical unit. Ascertaining a collision probability along a movement path of the robotic visualization system from a current pose to the ascertained target pose using a 3-D model of the surround. Ascertaining an adapted target pose for capturing an image corresponding to the target field of view with a second imaging configuration of the imaging optical unit using the 3-D model of the surround, should the ascertained collision probability exceed a predetermined threshold value.

15 Claims, 10 Drawing Sheets

METHOD FOR OPERATING A ROBOTIC VISUALIZATION SYSTEM, AND ROBOTIC VISUALIZATION SYSTEM

CROSS-REFERENCE TO RELATED APPLICATIONS

The present application claims priority under 35 U.S.C. § 119 to German Patent Application No. 10 2022 107 818.3, filed Apr. 1, 2022, the contents of which are incorporated by reference herein in their entirety.

SUBJECT MATTER OF THE INVENTION

The present invention relates to a method for operating a robotic visualization system, RVS, in particular for avoiding collisions of the RVS with static and/or dynamic objects in a surround of the RVS. The present invention also relates to a robotic visualization system, RVS, configured to carry out the method according to the invention and having at least an imaging optical unit and a robotic arm configured to position the at least one imaging optical unit.

TECHNOLOGICAL BACKGROUND

The use of technological aids is part and parcel of modern medicine. By now, imaging methods and robotic systems are used equally as a matter of course in both surgery and diagnostics. In this context, the use of imaging methods allows the display and discrimination of various structures in the patient and the image data obtained from the patient can be used advantageously in diagnostics and also in therapeutic and surgical methods.

By way of example, image data of a patient not only allows a surgeon to plan a surgical intervention better, but also assists them in performing the intervention. Robotic visualization systems are used to assist surgeons when performing surgical interventions. Said systems generally comprise a camera for recording images of the region to be operated on, with said camera being carried by a stand with an articulated structure. The carrier allows the camera to be positioned relative to the subject by way of translational and/or rotational movements, in order to capture images of a desired field of view (FOV) of the region to be operated on. The positioning into the capture pose can be implemented without manual intervention if the carrier comprises actuators.

The user regularly does not define the capture pose of the camera or carrier itself, but instead defines the desired field of view of the region to be operated on. This can be implemented in different ways, for example by aligning a projected marking on the region to be operated on, and deriving the field of view with computer assistance. The prior art has also disclosed the ascertainment of the field of view by detecting the viewing direction and, optionally, head movements of the user. The selection of the field of view by the user in a depiction of a larger field of view is also conceivable.

It is likewise known for there to be a computer-assisted avoidance of collisions of the camera and/or of the carrier with objects and/or subjects in the surround of the RVS during the automatic positioning of said RVS. As a rule, there is a definition of regions in which objects or subjects are situated, and a movement of the RVS into these regions is prevented. However, the regions defined thus disadvantageously restrict the capture poses which the RVS can adopt, and consequently not all desired fields of view are realizable with the RVS under certain circumstances. This is especially the case if a desired capture pose of the RVS cannot be adopted without a collision when the degrees of freedom of the RVS are taken into account, that is to say if there is no collision-free movement path to the desired capture pose. In particular, the user therefore finds in these cases that there is a significantly reduced usability of the RVS in relation to the capture of desired fields of view.

The object of the present invention is to overcome the disadvantages of the prior art and to provide an improved robotic visualization system.

DESCRIPTION OF THE INVENTION

The object according to the invention is achieved by the subjects of the independent patent claims. Preferred developments are the subject matter of the dependent claims.

A first aspect of the present disclosure relates to a method for operating a robotic visualization system, RVS, which comprises an imaging optical unit and a robotic arm for positioning the imaging optical unit. The imaging optical unit is fastened to the robotic arm. The imaging optical unit preferably is a camera or an eyepiece of a surgical microscope. The imaging optical unit particularly preferably is a camera with a zoom lens. Predominantly for reasons of legibility, the following description always refers to a camera as a representative for the imaging optical unit without, however, being restricted thereto. The robotic arm comprises at least two arm sections, which are connected byway of a joint, and is configured to enable translational and/or rotational movements of the camera. Preferably, the robotic arm comprises a plurality of arm sections, which are connected to one another by way of joints, and enables movements along/about at least 3 rotational and translational axes. The robotic arm is configured to position the camera in a surround.

A target field of view to be captured by means of the camera is initially ascertained within the scope of the method according to the invention. By way of example, this is preferably implemented on the basis of a user input, by means of which a target field of view, for example a region to be operated on, is defined. By way of example, the user input is implemented by marking the target field of view using a projected marking, by traversing the target field of view with a pointer having a tip that is localizable in space, by selecting the target field of view in a depiction of a larger field of view, and/or by detecting the viewing direction or head movement of a user, optionally in combination with a further (voice) command at the start of said user input.

Once the target field of view to be captured is known, a target pose of the RVS for capturing an image of the target field of view with a first imaging configuration of the camera is ascertained in the method according to the invention. In this case, the target pose of the RVS defines a spatial pose of the RVS, in particular of the camera of the RVS, the spatial pose allowing an image of the target field of view to be recorded by the camera and with the first imaging configuration. The target pose is a pose that is adoptable by the RVS, with the totality of adoptable poses being determined by the geometry of the RVS, the number of rotational/translational degrees of freedom, and the associated rotation or pivot regions. In this case, the spatial position denotes the position and the alignment of the RVS, in particular of the camera. The imaging configuration defines optical settings of the camera, for example a focal length and/or a zoom level of the camera. However, beyond this, the imaging configuration may also define further settings of the camera.

By way of example, if the camera comprises a plurality of lens elements or lenses, the imaging configuration preferably defines a chosen lens element or a chosen lens. The imaging configuration also preferably defines a digital zoom and/or image cropping.

By way of example, the first imaging configuration is a current imaging configuration of the camera. However, the first imaging configuration may also be the first of a plurality of possible imaging configurations. It is essential to the invention that the combination of ascertained target pose and first imaging configuration allows, in principle, the capture of an image of the target field of view, preferably in accordance with predetermined or user-defined requirements in respect of an image quality of the captured image, for example in respect of resolution, lighting, contrast or the like.

A collision probability along a movement path of the RVS from its current pose to the ascertained target pose is determined using a 3-D model of the surround in a further step of the method according to the invention. In this case, the ascertained target pose is part of the movement path of the RVS from its current pose to the ascertained target pose, and so a possible collision of the RVS at the ascertained target pose is likewise included in the collision probability. In particular, a probability of a collision of an element of the RVS, for example the camera or robotic arm, with an object and/or subject in the surround of the RVS is ascertained. By way of example, this is implemented by ascertaining a path of the RVS from the current pose to the target pose, or by ascertaining a channel of movement adopted by the RVS along this path, and the comparison thereof with the spatial regions adopted by the objects and/or subjects in the surround. These spatial regions may be geometrically simplified in the case of objects and/or subjects with a complex geometry, and a collision probability may also depend on the degree of the geometric simplification. In the case of dynamic objects and/or subjects, the spatial regions may be extrapolated on the basis of current positions and velocities of the objects and/or subjects, and a collision probability may also depend on the extrapolation. A person skilled in the art knows of the options for ascertaining a collision probability using a 3-D model of the surround. Exemplary configurations of such a model or such a collision ascertainment are described below. In the process, the collision probability may be ascertained as a binary number or floating-point number. In principle, the RVS may also collide with itself, and such a collision probability is likewise taken into account. However, the poses that are assumable by the RVS are preferably defined in such a way that there is no collision of the RVS with itself in such a pose or along a movement path between such poses.

Should the ascertained collision probability exceed a predetermined threshold value, an adapted target pose of the RVS for capturing an image, which corresponds to the target field of view, with a second imaging configuration of the camera is ascertained in the method according to the invention, once again using the 3-D model of the surround. Expressed differently, a combination of adapted target pose and second imaging configuration, which allows the capture of an image corresponding to the target field of view, is ascertained in the method according to the invention. In this case, too, predetermined or user-defined requirements in respect of an image quality of the captured image, such as resolution, lighting, or contrast, are preferably taken into account. The adapted target pose is also a pose that is adoptable by the RVS, with the totality of adoptable poses being defined by the geometry of the RVS, the number of rotational/translational degrees of freedom, and associated rotation or pivot regions.

What can advantageously be ensured here by means of the 3-D model of the surround is that the adapted target pose is reachable from the current pose via a collision-free movement path of the RVS. By way of example, the method according to the invention can be repeated recursively with the adapted target pose as the ascertained target pose until the movement path from the current pose of the RVS to the adapted target pose ascertained in the last recursion is collision free, that is to say has a collision probability below a predefined threshold value. The 3-D model is preferably used explicitly or implicitly when ascertaining the adapted target pose. By way of example, an implicit use of the 3-D model is implemented in the form of a boundary condition for verifying the freedom of collisions of already ascertained adapted target poses. By way of example, an explicit use includes the use of the freedom of collisions of an adapted target pose, ascertained by means of the 3-D model, as a feature $x_i$ of this target pose in a cost function, as will be described in detail below.

The method according to the invention therefore advantageously allows an image of the desired target field of view to be recorded, while simultaneously avoiding collisions of the RVS with objects and/or subjects in the surround thereof. The method according to the invention consequently represents a method for avoiding collisions, in which the optical imaging configuration of the RVS is used as an additional degree of freedom for ascertaining a collision-free path of the RVS. In contrast to known methods, in which the freedom of movement of the RVS and hence the possible target fields of view are restricted, the method according to the invention allows the user to image virtually any target field of view while simultaneously ensuring collision-free movements of the RVS.

In a preferred implementation, the method according to the invention further includes the step of ascertaining an adapted movement path to the initially ascertained target pose. There particularly preferably is an ascertainment as to whether the initially ascertained target pose is reachable via an alternative and collision-free movement path. In this case, the alternative movement path may have, for example, a longer displacement path and/or displacement time than the initially ascertained movement path from the current pose of the RVS to the initially ascertained target pose. Consequently, a preferred implementation initially includes an ascertainment as to whether the desired target pose can be reached collision-free using an alternative movement path, and an adapted target pose is only ascertained in the case where this is not possible. Alternatively, an adapted movement path and an adapted target pose (with a corresponding second imaging configuration) are ascertained in parallel and one of the adapted movement path and the adapted target pose is selected on the basis of additional parameters, for example on the basis of a comparison of an additional displacement time along the adapted movement path with a limit value. The method according to the invention advantageously allows an image corresponding to the target field of view to be recorded, even in cases in which the initially ascertained target pose cannot be reached collision-free along any (initially ascertained/alternative) movement path. Moreover, the method according to the invention provides a further degree of freedom of the RVS for capturing an image corresponding to a target field of view to be visualized.

In a preferred implementation of the method according to the invention, the second imaging configuration has an adapted focal length in comparison with the first imaging configuration. Expressed differently, the camera has a different distance between the lens and the field of view imaged sharply on the sensor or the focus in the second imaging configuration vis-à-vis the first imaging configuration. In this case, the focal length of the second imaging configuration preferably corresponds to an adapted vertical distance between camera and target field of view in the adapted target pose. Likewise preferably, the second imaging configuration has an adapted zoom level in comparison with the first imaging configuration. Expressed differently, the camera has a different focal length in the second imaging configuration vis-à-vis the first imaging configuration. In this case, the focal length of the second imaging configuration preferably corresponds to the vertical distance between the camera and target field of view in the adapted target pose, but this is not mandatory, especially if a zoom lens is used. Advantageously, a recording of the target field of view equivalent to that obtained in the target pose with the first imaging configuration is able to be captured in the adapted target pose with the second imaging configuration.

To the extent that the second imaging configuration has an adapted zoom level in comparison with the first imaging configuration, this is preferably achieved by way of an optical zoom of a zoom lens and/or a digital zoom. A digital zoom essentially is the choice of an image section of the current field of view that corresponds to a desired target field of view and the enlarged depiction of said image section, optionally at a lower resolution in comparison with the depiction of the current field of view. In both implementations, that is to say with optical zoom or with digital zoom, the adapted target pose may therefore optionally also be the current pose of the RVS. By way of example, this may be the case where the initially ascertained target pose is only shifted from the currently ascertained target pose along the optical axis of the camera, but there is the risk of a collision as a result of this shift, and a zoom operation still allows an image corresponding to the target field of view to be recorded. Should a digital zoom be used, the image corresponding to the target field of view may optionally have a lower resolution, but is in return able to be captured without collision in the method.

Further preferably, the adapted target pose is shifted vis-à-vis the target pose in the normal direction of the target field of view. Particularly preferably, the adapted target pose is only shifted in the normal direction of the target field of view vis-à-vis the target pose and is not tilted in relation to the normal direction. Likewise preferably, the previously ascertained target pose is not tilted in relation to the normal direction of the target field of view. Expressed differently, the optical axis of the camera in the previously ascertained target pose is parallel to a normal direction of the target field of view and the adapted target pose is (only) shifted along the optical axis of the camera vis-à-vis the previously ascertained target pose. Advantageously, all change of pose-related deviations of the field of view depicted by the camera from the target field of view are consequently compensable by adapting the focal length and/or zoom level of the camera. In particular, equivalent fields of view are realizable by various combinations of the pose of the RVS, zoom level, and focal length. The target pose and the first image configuration and the adapted target pose and the second image configuration advantageously realize such equivalent fields of view with the camera.

In a preferred implementation, the method according to the invention moreover comprises the method step of positioning the camera in the adapted target pose with the robotic arm. Positioning the camera in the adapted target pose preferably comprises a translation and/or rotation of the camera by means of the robotic arm, particularly preferably only a translation. Positioning the camera into (in) the adapted target pose is also preferably implemented if it is ascertained that a collision probability, ascertained using the 3-D model of the surround, along a movement of path of the RVS from the current pose of the RVS to the ascertained adapted target pose drops below a predetermined threshold value. In other words, the method according to the invention preferably includes the ascertainment of a collision probability along a movement path of the RVS from the current pose of the RVS to the adapted target pose using a 3-D model of the surround. This advantageously ensures that an adapted target pose that allows an equivalent field of view is homed in on without collisions with subjects and/or objects in the surround.

Likewise preferably, the method according to the invention additionally includes the method step of capturing, with the second imaging configuration, the image of the target field of view corresponding to the target field of view. The capture of the image corresponding to the target field of view is implemented by means of the camera and, advantageously according to this implementation, of the target field of view itself. Consequently, there is no deviation between the desired target field of view and the field of view depicted in the captured image, and the user is ultimately provided with an image of precisely the desired target field of view. The depiction of the image is implemented, for example, in enlarged fashion and/or with an overlay of 3-D patient data captured using other imaging methods, for example MRI. The image is preferably depicted by means of a screen of the RVS or by means of a piece of visual output equipment worn by the user on their head (Head-Mounted Display—HMD).

In a particularly preferred implementation of the method according to the invention, the step of ascertaining the adapted target pose of the RVS includes a plurality of method steps carried out conditionally and successively. Accordingly, in a first step (a), a collision-free movement path to an adapted target pose only shifted from the (previously ascertained) target pose in the normal direction of the target field of view or along the optical axis of the camera (in the previously ascertained target pose) is ascertained. In particular, a check is carried out as to whether there is an adapted target pose which has only been shifted along the optical axis and in which an image of the desired target field of view is capturable with a second imaging configuration that is realizable by the camera and to which there is a collision-free movement path of the RVS from the current pose of the RVS. If such an adapted target pose is ascertained, the camera is positioned in this adapted target pose by means of the robotic arm and an image of the target field of view is captured therein. Advantageously, this image is an image of the (previously ascertained) target field of view chosen by the user.

If such an adapted target pose which has merely been shifted in the normal direction of the target field of view is not ascertainable, there is, in a further method step (b), the ascertainment of a collision-free movement path to an adapted target pose with an optical axis of the camera that has been pivoted vis-à-vis the target pose. Consequently, this method step is carried out if it had not been possible to ascertain an adapted target pose which has merely been shifted in the normal direction of the target field of view and in which an image of the target field of view is capturable with the second imaging configuration. In the method step, a check is carried out, in particular, as to whether there is an adapted target pose which has a pivoted optical axis of the camera vis-à-vis the target pose and in which an image corresponding to the target field of view is capturable with a second imaging configuration that is realizable by the camera and to which there is a collision-free movement path of the RVS from the current pose of the RVS. The adapted target pose may have a pivoted optical axis of the camera vis-à-vis the target pose and, moreover, may be shifted vis-à-vis the target pose in the normal direction of the target field of view. If an adapted target pose is ascertained in this method step, the camera is positioned in this adapted target pose by means of the robotic arm and an image corresponding to the target field of view is captured.

If such an adapted target pose which has a pivoted optical axis of the camera vis-à-vis the target pose, which is able to be reached without collisions, and in which an image corresponding to the target field of view is capturable is not ascertainable, there is, in a further method step (c), the ascertainment of a collision free movement path to an adapted target pose with a shifted optical axis of the camera vis-à-vis the target pose. Preferably, this step, too, is only carried out if method step (b) has not supplied a result. In the method step, a check is carried out, in particular, as to whether there is an adapted target pose which has a shifted optical axis of the camera vis-à-vis the target pose and in which an image corresponding to the target field of view is capturable with a second imaging configuration that is realizable by the camera and to which there is a collision-free movement path of the RVS from the current pose of the RVS. The adapted target pose may have a shifted optical axis of the camera vis-à-vis the target pose and the optical axis may also be pivoted and/or the adapted target pose may also be shifted vis-à-vis the target pose in the normal direction of the target field of view. If an adapted target pose is ascertained in method step (c), the camera is positioned in the adapted target pose by means of the robotic arm and an image corresponding to the target field of view is captured. If no adapted target pose is able to be found in method step (c) either, the method is terminated and no image of the target field of view is capturable.

According to this particularly preferred implementation of the method according to the invention with successively and conditionally carried out partial steps, an image of the target field of view is advantageously recorded and an image of an adapted field of view which overlaps with the target field of view, which image corresponds to the target field of view, is recorded only if this is not possible (method step (a) supplies no result). In this case, an overlap (a correspondence) of the adapted field of view in an adapted target pose ascertained in method step (b) regularly exceeds the overlap or the correspondence of the adapted field of view in an adapted target pose ascertained in method step (c). By virtue of step (c) only being carried out if step (b) supplies no result, an image corresponding best to the target field of view is advantageously captured.

In a further preferred implementation, the actual or expected quality in view of the desired target field of view of the image capturable in the adapted target pose, inter alia, is described by a cost function. According to this implementation, ascertaining the adapted target pose of the RVS includes the steps set forth below. Initially, (a plurality of) collision-free movement trajectories from the current pose to a plurality of possible adapted target poses are ascertained, with each of the adapted target poses, in principle, being suitable for the capture of an image, corresponding to the target field of view, with a second imaging configuration of the camera. In other words, this step also contains the ascertainment of the plurality of possible adapted target poses.

For each of the possible adapted target poses, a value of a target function characterizing the adapted target pose is subsequently ascertained on the basis of features $x_i$ of said adapted target pose. In this case, the features $x_i$ of the target pose can relate to both the quality of the image capturable in the target pose and other features, as described below. Finally, one of the adapted target poses ascertained as possible is selected on the basis of the ascertained characterizing values of the target function. In particular, one of the adapted target poses having a characterizing value corresponding to a local or global extremum of the target function is selected. In this case, ascertaining the characterizing value preferably comprises the ascertainment of a weighted sum $\Sigma g_i x_i$ of features $x_i$ of the adapted target pose, as described below. Alternatively preferably, the local or global extremum of the target function or the characteristic value corresponding thereto is ascertained by means of the gradient method, by way of geometrically solving the corresponding linear system of equations, by way of directly geometrically ascertaining intersections, and/or under the assumption of virtual forces.

According to an exemplary preferred implementation of the method according to the invention, the characterizing value is ascertained on the basis of a weighted sum $\Sigma g_i x_i$ of features $x_i$ of the adapted target pose. In this case, a first weight $g_1$ corresponds to a feature $x_1$, according to which the adapted target pose is reachable vis-à-vis the target pose by shifting the camera in the normal direction of the target field of view (or along the optical axis of the camera in the target pose). A second weight $g_2$ corresponds to a feature $x_2$, according to which the adapted target pose is reachable by pivoting the optical axis of the camera vis-à-vis the target pose, and a third weight $g_3$ corresponds to a feature $x_3$, according to which the adapted target pose is reachable by shifting the optical axis of the camera vis-à-vis the target pose. The features $x_1$ to $x_3$ are preferably quantitative features. By way of example, feature $x_1$ defines the number of shifts along the optical axis by a predefined length (for example 10 cm) and the weight $g_1$ preferably relates to the predefined length. Likewise preferably, the feature $x_2$ defines the number of degrees through which the optical axis of the camera is pivoted in order to reach the adapted target pose, and the weight $g_2$ relates to a pivoting through one degree. Preferably, feature $x_3$ defines the number of shifts transversely (orthogonally) to the optical axis by a predefined length (for example 10 cm) and weight $g_3$ relates to this predefined length.

Particularly preferably, the third weight $g_3$ is greater than the second weight $g_2$, and the second weight $g_2$ is greater than the first weight $g_1$. According to this implementation, the characterizing value of the selected adapted target pose preferably represents a local or global minimum of the target function. Alternatively preferably, the third weight $g_3$ is less than the second weight $g_2$, and the second weight $g_2$ is less than the first weight $g_1$. According to this implementation, the characterizing value of the selected adapted target pose preferably represents a local or global maximum of the target function.

According to these preferred implementations, it is consequently advantageously possible to ascertain the collision-free adapted target pose (characterized by the RVS pose and imaging configuration) in which an image of a field of view which is "the most similar" to the desired target field of view is capturable. In this case, this "similarity" is assessed by said target function (cost function) and has the "most similar" adapted target pose, for example the smallest value of the target function (the lowest costs). In this case, a pure focus adaptation, that is to say shifting the camera along the optical axis, is weighted lowest, an orientation error, that is to say the pitching or yawing (pivoting) of the optical axis is weighted higher, and a position error, that is to say (lateral) shifting of the adapted field of view with respect to the desired target field of view, is weighted highest. Advantageously, a collision-free target pose, which enables an image of a field of view that is as "similar" as possible, is found in this way. If the cost function is implemented purely with the features $x_1$, $x_2$, and $x_3$, as described above, this yields a similar result as the likewise preferred implementation with the above-described successive and conditional partial steps.

Moreover, however, the cost function advantageously allows taking account of further features of the adapted target pose in the form of features $x_i$ of the adapted target pose. These features $x_i$ further preferably comprise an adjustment of the imaging configuration of the camera. If the latter is provided with a weight greater than zero, there consequently is a preference for target poses which do not render necessary an adjustment of the imaging configuration of the camera or which require the smallest possible adjustment of said imaging configuration. In this implementation (and generally within the scope of the present disclosure), the first imaging configuration preferably corresponds to the current imaging configuration of the camera. The ascertained target pose would consequently render possible the capture of an image of the target field of view without adjusting the imaging configuration, but cannot be homed in on due to the probable collision.

Likewise preferably, the features $x_i$ comprise a height of the camera and/or of the RVS, or an adaptation of same. The weight of the height may vary in the process, for example the weights are chosen so that a constant height is preferred. The weights are likewise preferably chosen so that an undershoot of a minimum height is avoided, with this minimum height for example exceeding the size of a user, in order to also further reduce the probability of collisions in this way. The weights are likewise preferably chosen so that an overshoot of a maximum height is avoided, with this maximum height for example corresponding to the height of fixed objects in the surround of the RVS, for example ceilings or luminaires fastened thereto.

The features $x_i$ further preferably comprise a displacement time and/or a displacement path of the RVS from the current pose to the adapted target pose. In this case, the weights will generally have been set so that a shortest possible displacement time or displacement path is preferred. In the simplest case, this is achieved by setting positive weights $g_i$ and ascertaining the characteristic value as a minimum of the target function.

Likewise preferably, the features $x_i$ comprise a distance between the camera and the target field of view. In this case, the weights $g_i$ can be chosen so that a smallest possible such working distance is preferred. As a rule, this is advantageous in that an image with a higher resolution is obtained and in that desired pivoting of the field of view is realizable with a short displacement time (displacement path). Moreover, in the case of stereo cameras, information relating to the parallax is better detectable in the case of short working distances. Such weighting is conceivable, in particular in combination with a weighting of the feature of the height of the RVS. However, vertical minimum distances from the head of the user, etc., are also realizable by way of the working distance feature or the choice of suitable weights.

Likewise preferably, the features $x_i$ comprise user-defined boundary conditions, which reflect personal preferences of the user and which, in principle, may relate to any of the aforementioned features, that is to say, for example, the height of camera/RVS, the displacement time (displacement path), the working distance of camera and target field of view or further features $x_i$ of the target pose. By way of example, a first user may prefer a greater working distances in order to perceive as few of the movements of the RVS as possible and will accept a lower resolution in return, while the second user may prefer a higher resolution and is not irritated by the RVS moving within their visual field.

Further preferably, the features $x_i$ of the adapted target pose comprise a collision probability from the current pose of the camera to the adapted target pose. Consequently, the collision probability is not ascertained separately from the ascertainment of the "similarity" of the adapted target pose, but is likewise mapped by the target function. Ascertaining an adapted target pose with a value of the target function characteristic for an extremum of the target function consequently advantageously automatically leads to the ascertainment of an adapted target pose which can be reached without collisions. This is preferably achieved by linking the target function to the 3-D model of the surround, that is to say for example by transferring a value regarding the currently considered adapted target pose from the target function to the 3-D model, by means of which the simulation of the movement path is implemented, and transferring a value relating to the collision probability from the 3-D model to the target function. The collision probability has to be weighted positively in the case of the characteristic value as a minimum of the target function.

In a preferred implementation of the method according to the invention, the 3-D model of the surround defines at least one region that is blocked for the RVS. The use of three-dimensional modeling of the surround for identifying possible collisions is just as essential for the method according to the invention as the control of the motor-driven movement of the RVS in view of the modeling and the requirements in respect of the field of view The three-dimensional model preferably comprises a three-dimensional representation of the workspace of the RVS and is modeled by a user and/or is based on a sensor-assisted detection of the surround. By way of example static objects in the surround, such as walls, ceilings, floors and fixed furnishings, are modeled and dynamic objects, such as persons or movable articles, are modeled on the basis of a sensor-assisted detection of the surround. However, static objects in the surround are preferably also based on a scan or an image representation of the surround. The 3-D model of the surround further preferably comprises a 3-D model of the RVS or at least permits the integration (combination) of a 3-D model of the RVS. A person skilled in the art is aware of various methods for creating 3-D models and, in principle, any 3-D model which allows the ascertainment of collision probabilities along trajectories within the 3-D model is usable in the method according to the invention.

In a preferred implementation of the method according to the invention, the 3-D model of the surround represents static and dynamic objects within the surround as simple (primitive) 3-D shapes. By way of example, the model uses planes for walls, ceilings, and floors, and cuboids and ellipsoids for static or dynamic objects. Likewise preferably, the 3-D model of the surround represents the RVS as a simple (primitive) 3-D shape or as a shape composed of simple (primitive) 3-D shapes. Consequently, both the static surround and dynamic objects in the surround and the RVS itself, as well as the movements of same, can be described within the 3-D model by simple (primitive) 3-D shapes, which advantageously increases the computational efficiency of the model.

As an alternative or in addition to mathematical modeling with primitive shapes, the 3-D model is based on a sensor-assisted detection of the surround. Particularly preferably, the 3-D model is based on acquired depth data of the surround, acquired by means of a stereo camera, time-of-flight, TOF, camera systems, lidar systems, and/or systems for structured light scanning. Likewise preferably, the 3-D model is based on a combination of sensor-assisted detection and modeling using simple shapes, by virtue of the static and dynamic objects in the surround initially being detected and subsequently being approximated using primitive shapes. Further preferably, a kinematic model of the RVS on the basis of primitive shapes is integrated into the 3-D model of the surround. In this case, the surround is preferably modeled before the collision probability is ascertained. Ascertaining the collision probability is preferably based on the simulation of the movement of the RVS in the 3-D model by means of the RVS model integrated therein. Particularly preferably, the model of the surround is updated regularly, even while the method according to the invention is carried out.

A further aspect of the present disclosure relates to a robotic visualization system, RVS, for use in medical operations. In this case, the RVS according to the invention comprises a camera with a zoom lens. The camera preferably is a stereo camera with a zoom lens. Likewise preferably, the RVS comprises a plurality of cameras, for example a main observer camera and a surround camera. The RVS further preferably comprises a robotic arm which is configured to position the at least one camera. The robotic arm comprises at least two arm sections, which are connected byway of a joint, and is configured to enable translational and/or rotational movements of the camera. Preferably, the robotic arm comprises a plurality of arm sections, which are connected to one another by way of joints, and enables movements along/about at least 3 rotational and translational axes.

The RVS according to the invention further comprises a control unit which is configured to control the camera and robotic arm. The control unit is further configured to carry out a method according to the invention as described above. In particular, the control unit is configured and designed to ascertain a target field of view to be visualized by means of the camera, ascertain a target pose of the RVS for capturing an image of the target field of view with a first imaging configuration of the camera, ascertain a collision probability along a movement path of the RVS from a current pose of the RVS to the ascertained target pose using a 3-D model of the surround, and ascertain an adapted target pose of the RVS for capturing an image corresponding to the target field of view with a second imaging configuration of the camera using the 3-D model of the surround, should the ascertained collision probability exceed a predetermined threshold value.

The RVS according to the invention further preferably comprises sensors configured for the three-dimensional detection of the surround. Particularly preferably, the RVS according to the invention comprises stereo cameras, time-of-flight, TOF, camera systems, lidar systems, and/or systems for structured light scanning for acquiring depth information of the surround. Additionally or alternatively, the control unit is designed to receive information regarding the three-dimensional structure of the surround, in particular depth information relating to the surround, from external sensors. By way of example, the external sensors are sensor systems that are fixedly installed in the surround of the RVS. Like the sensors of the RVS, these are preferably designed as a stereo camera, TOF camera, lidar, etc. The control unit of the RVS according to the invention is further preferably designed to create a 3-D model of the surround, for example using primitive shapes, on the basis of the depth information acquired by means of the sensors, on the basis of the depth information received from the external sensors, and/or on the basis of depth information loaded from a database or input by a user. The control unit of the RVS according to the invention is further designed to integrate a kinematic model of the RVS, which for example has been created by means of primitive shapes, into the 3-D model of the surround and use the integrated model to simulate movements of the RVS in the surround and ascertain collision probabilities on the basis thereof.

The functionalities of the control unit according to the invention can be implemented by electrical or electronic devices or components (hardware), by firmware (ASIC) and/or can be realized by carrying out a suitable program (software). Preferably, the functionalities of the control unit according to the invention are realized or implemented by a combination of hardware, firmware and/or software. By way of example, individual components of the control unit according to the invention for carrying out individual functionalities are in the form of a separately integrated circuit or are arranged on a common integrated circuit.

The individual functionalities of the control unit according to the invention are further preferably in the form of one or more processes which run on one or more processors in one or more electronic computers and which are generated when carrying out one or more computer programs. In this case, the control unit is designed to cooperate with other components, in particular the camera, and the robotic arm in order to implement the functionalities of the RVS according to the invention as described herein. It is further evident to a person skilled in the art that the functionalities of a plurality of computers (data-processing equipment, control units, controllers) can be combined or can be combined in a single piece of equipment, or that the functionality of one certain piece of data-processing equipment may be available distributed over a multiplicity of pieces of equipment in order to realize the functionalities of the control unit according to the invention.

In a particularly preferred embodiment of the RVS according to the invention, the latter is integrated in a surgical microscope. In this case, the surgical microscope preferably comprises a camera and a robotic arm with a calibrated kinematic system, which allows a defined rotation (x, y, z) and translation (x, y, z) of the camera fastened to the robotic arm. Preferably, the camera is a main observer camera or a surround camera of the surgical microscope. The control unit of the surgical microscope is preferably designed as control unit of the RVS according to the invention and, in particular, designed to carry out the method according to the invention, as described above, on the basis of commands stored on a storage unit of the surgical microscope.

Within the scope of the present disclosure, a surgical microscope is understood in the broadest sense to be a microscope suitable for use during an operation. The surgical microscope preferably has a mount which allows imaging of the operating region independently of head movements of the surgeon. Further preferably, the surgical microscope comprises at least one beam splitter and at least two eyepieces. Likewise preferably, the surgical microscope comprises at least one imaging sensor. Further preferably, the surgical microscope comprises a main observer camera and a surround camera. The surgical microscope may comprise kinematic or robotic aids for carrying out surgical interventions. As an alternative, a surgical microscope may be denoted a medical engineering microscope, a medically approved microscope or a medical microscope.

A further aspect of the present disclosure relates to a computer program comprising commands which, when executed by a control unit as described above, preferably of a surgical microscope or RVS as described above, cause the surgical microscope or RVS as described above to carry out the method according to the invention as described above. The computer program preferably comprises commands which, when executed by a control unit as described above, preferably of a surgical microscope or RVS as described above, cause the surgical microscope or RVS as described above to carry out the method according to the invention, in accordance with one of the preferred implementations, as described above. In this case, the computer program according to the invention is preferably stored in a volatile memory, for example a RAM element, or in a non-volatile storage medium, for example a CD-ROM, a flash memory or the like.

Further preferred embodiments of the invention will become clear from the other features set out in the dependent claims. The various embodiments of the invention that are set forth in this application can advantageously be combined with one another, unless specifically stated otherwise.

DESCRIPTION OF THE FIGURES

The invention is explained below in illustrative embodiments and with reference to the attached drawings, In the drawings.

14

Figure 1:
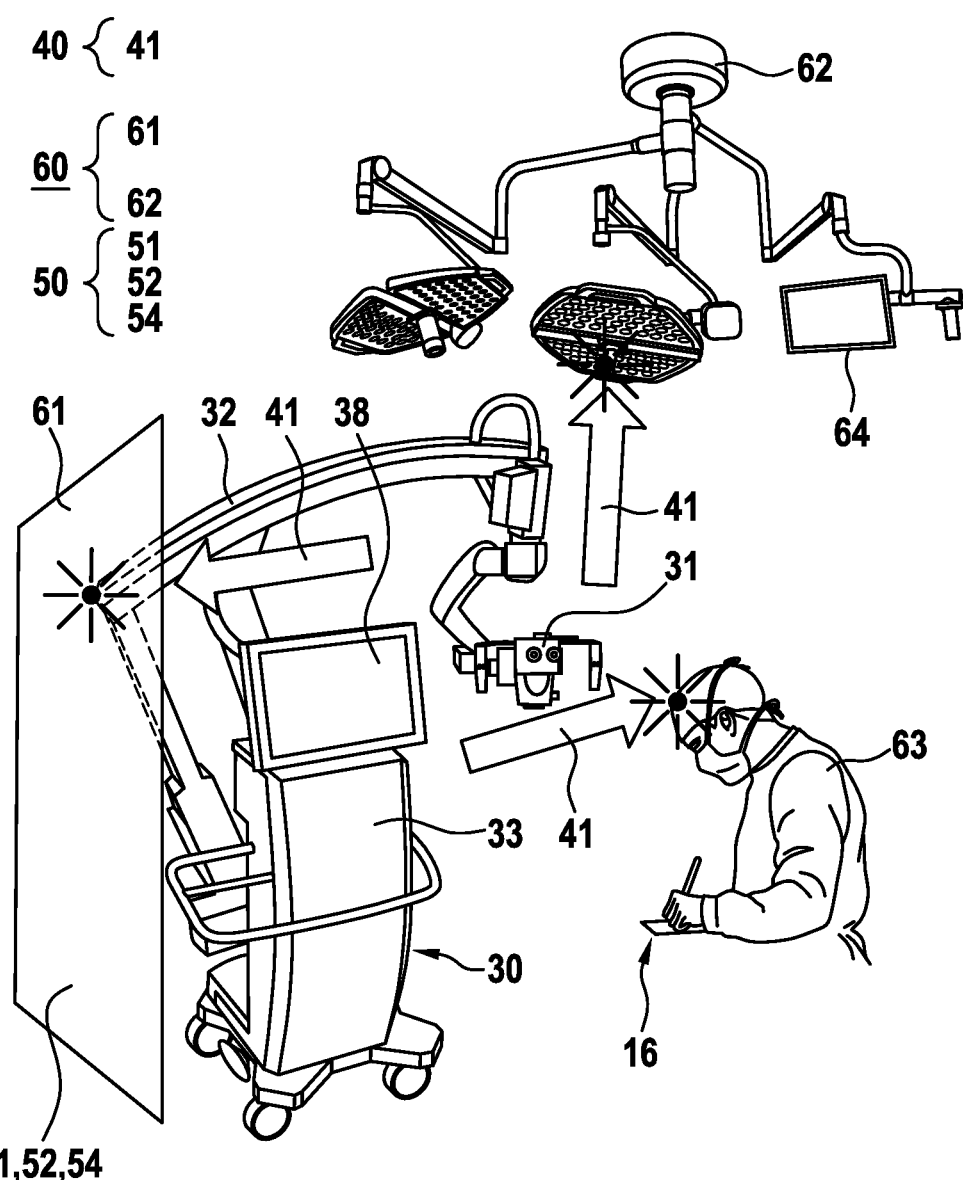
FIG. 1 shows a schematic representation of a robotic visualization system in a typical surround for the use thereof as a surgical microscope.

FIG. 1 shows a schematic representation of a robotic visualization system 30, RVS, in a typical surround 60 for the use thereof as a surgical microscope.

The RVS 30 is a surgical microscope comprising a camera 31, a robotic arm 32 and a control unit 33 which is arranged in a housing. The camera 31 has a zoom lens, by means of which it is possible to record images of a field of view of the camera in a focal plane. Images of the field of view of the camera 31 are transferred to the control unit 33, processed by the latter, and displayed on the screen 38. The magnification and the target field of view of the camera 31 can be adjusted by the control unit 33, which optionally controls the robotic arm 32 to this end.

The control unit 33 of the RVS 30 is arranged in a housing, on which the robotic arm 32 and the screen 38 are also arranged. The camera 31 can be positioned in the surround 60 by shifting the housing and by way of the robotic arm 32. The robotic arm 32 is configured, under control of the control unit 33, to carry out both translational movements in three independent directions and rotational movements about three independent axes. In particular, the camera 31 can be positioned by means of the robotic arm 32 so that the field of view of the camera 31 corresponds to an operating region 16, in which a user 63 carries out an operation. On the screen 38, the user 63 can observe the images of the operating region 16 transferred by the control unit 33. The images displayed on the display 38 are images which were recorded by the camera 31 and processed (for example, by cropping, rotating, improving the contrast, correcting the color, etc.). Alternatively, the user may also observe the images on a further screen 64.

The surround 60 of the RVS 30 shown in FIG. 1 contains a plurality of objects, with which the RVS 30 can collide, in addition to the user 63. In this case, the objects comprise static objects, for example a wall 61, and also dynamic objects, for example a ceiling-mounted mount 62 for a luminaire and the further screen 64. When the camera 31 is positioned in the surround 60 by means of the robotic arm 32, there is a risk of collisions with these dynamic or static objects 61, 62 and with the user 63. In FIG. 1, this is represented by a plurality of potential movement trajectories 41, along which the RVS 30, in particular camera 31 or robotic arm 32, collides with the dynamic or static objects 61, 62 or with the user 63. According to the prior art, such collisions are avoided by virtue of certain spatial regions being blocked to the movement of the RVS 30. However, this disadvantageously restricts the degrees of freedom of the RVS 30, and hence also possible fields of view of the camera 31.

Figure 2:
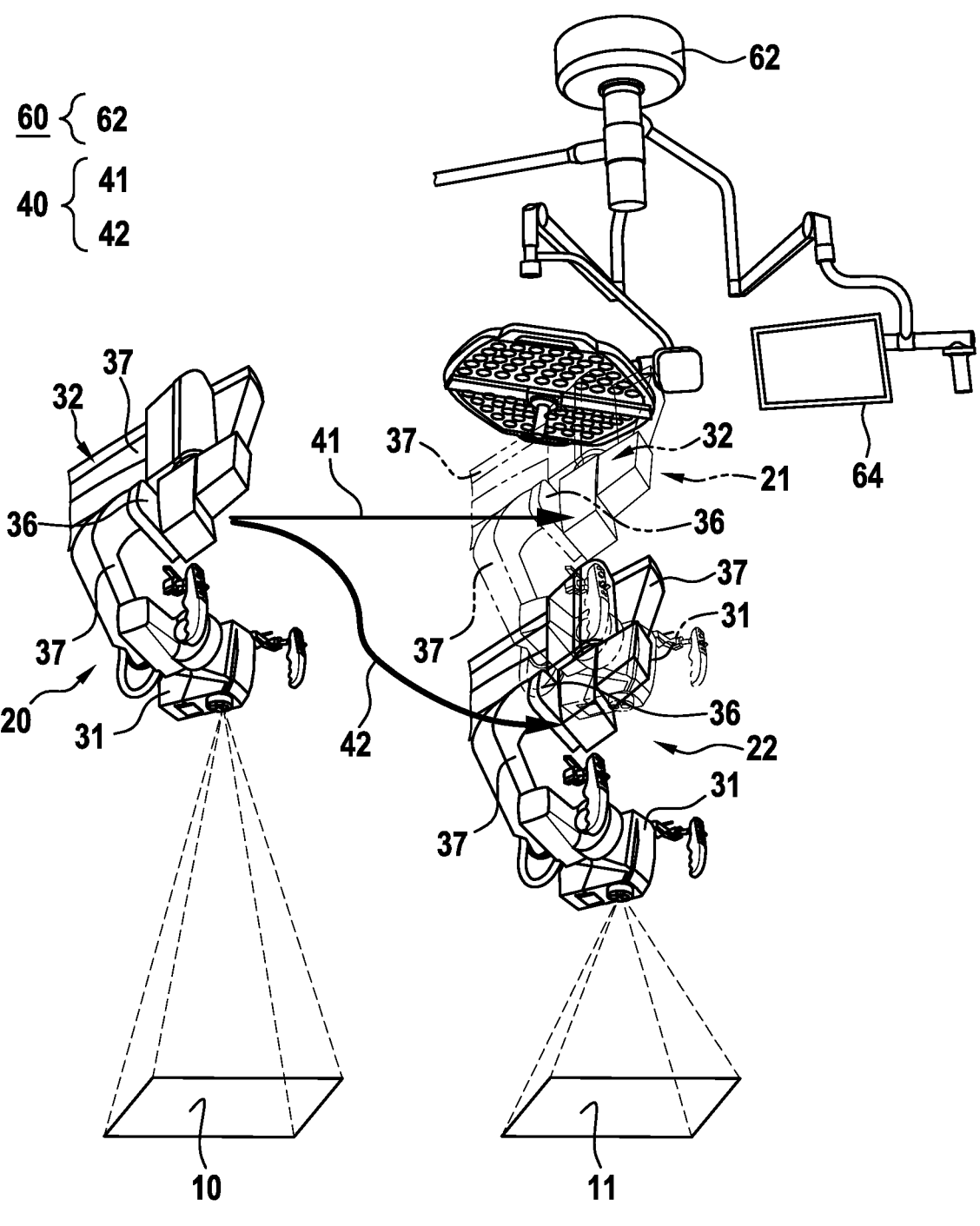
FIG. 2 shows a representation of an operation of the robotic visualization system according to an implementation of the method according to the invention.

FIG. 2 shows a representation of an operation of the robotic visualization system 30, RVS, according to an implementation of the method according to the invention.

The RVS 30 corresponds to that shown in FIG. 1, but only the camera 31 and the robotic arm 32 are presented in detail for reasons of clarity. As can be identified better in FIG. 2, the robotic arm 32 comprises a plurality of arm sections 37, which are interconnected by way of joints 36. The left-hand side of FIG. 2 shows the RVS 30, especially the camera 31 and the robotic arm 32, in a current pose 20. A field of view 10 currently captured by the camera 31 corresponds to the current pose 20.

Based on a user input, the intention is to capture a target field of view 11 with the camera 31 and, for example, present an image representation thereof on the screen 38. A target pose 21 of the RVS 30, in which the RVS 30 is depicted in FIG. 2 using dashed lines, corresponds to the target field of view 11. In this target pose 21, an image of the target field of view 11 is able to be captured with the current imaging configuration of the camera 31. Consequently, only the position of the camera 31 needs to be adapted from the current pose 20 to the target pose 21 by means of the robotic arm 32 in order to record an image of the target field of view 11. There would be no need to adapt the imaging configuration, in particular the zoom and focal length.

As depicted in FIG. 2, a collision between the RVS 30 and a mount 62 for a luminaire and a further screen 64 would arise along the movement path 41 from the current pose 20 to the target pose 21. Therefore, an adapted target pose 22 is ascertained in the method according to the invention, in which target pose an image of the desired target field of view 11 is likewise able to be captured by the camera 31 and which target pose is reachable from the current pose 20 without collision along an adapted movement path 42. An adaptation of the current imaging configuration of the camera 31 is required to be able to capture an equivalent image of the target field of view 11 in the adapted target pose 22. In the method according to the invention, this adaptation is carried out in order to be able to record an image of the target field of view 11 with an adapted imaging configuration in the adapted target pose 22.

Figure 3A:
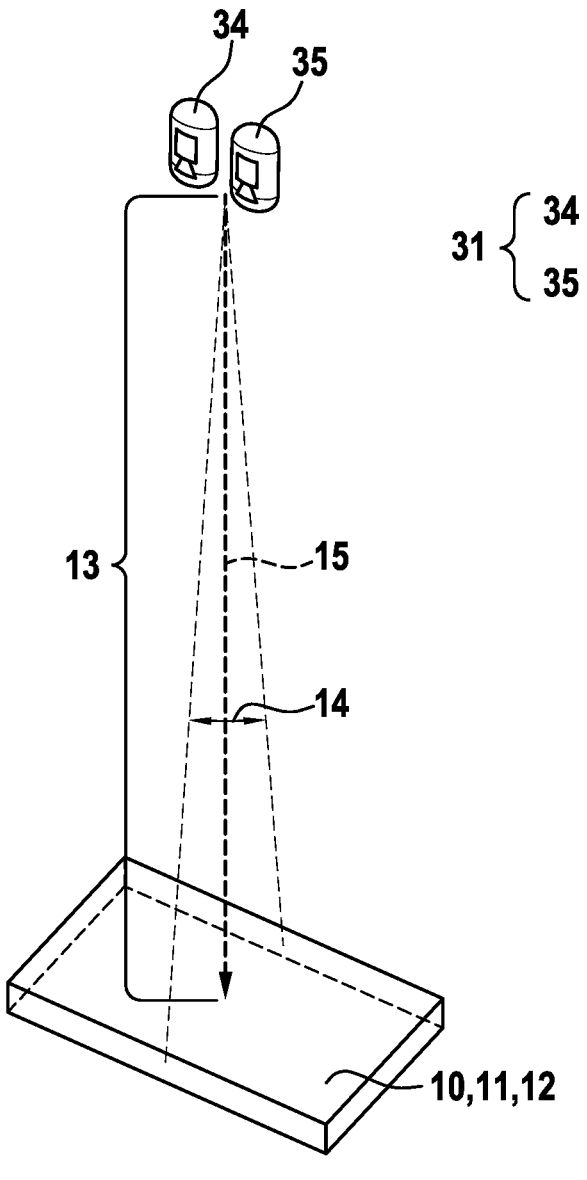
FIG. 3A shows a schematic representation of the field of view and imaging configuration of the robotic visualization system.

FIG. 3A shows a schematic representation of the relationship between field of view 10, 11, 12 and imaging configuration of the camera 31 of the robotic visualization system 30. In this case, the camera 31 is a stereo camera comprising a first camera 34 and a second camera 35. However, for simplification, FIG. 3A represents the optical properties of the camera 31 for only one of the cameras 34 and 35. As depicted in FIG. 3A, the imaging configuration of the camera 31 is determined, inter alia, by a focal length 13 and a zoom level 14. In this case, the focal length 13 denotes the distance between the camera 31 and field of view 10, 11, 12 along an optical axis 15 of the camera 31, and the zoom level 14 denotes an aperture angle of a beam captured by the camera 31, which aperture angle is required to image the entire field of view 10, 11, 12. It is already evident from FIG. 3A that a combination of the pose, the focal length 13, and the zoom level 14 of the camera corresponds to a specific field of view 10, 11, 12. Since the camera 31 is fastened to the robotic arm 32, this relates to a pose of the RVS 30.

Figure 3B:
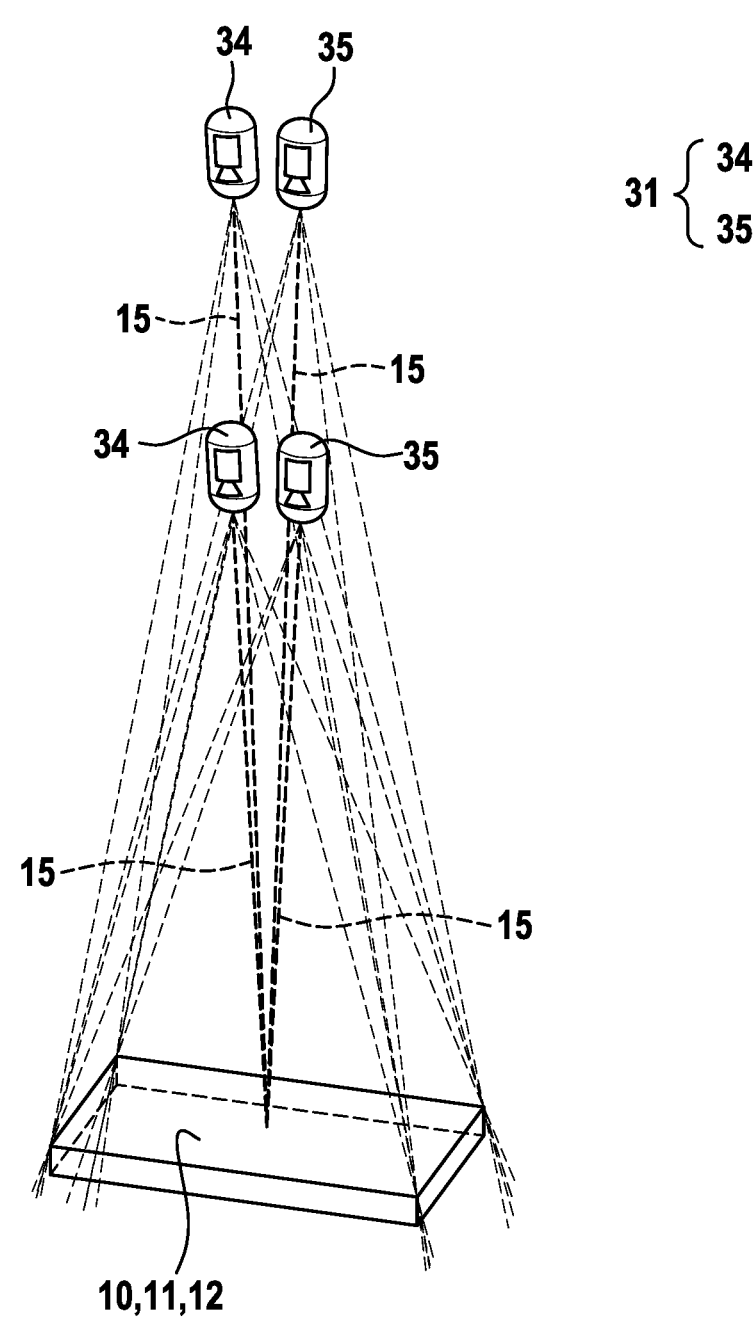
FIG. 3B shows a schematic representation of the field of view and of first and second imaging configuration of the robotic visualization system.

FIG. 3B shows a schematic representation of the relationship between field of view 10, 11, 12 and imaging configuration of the camera 31 of the robotic visualization system 30 in a first and a second imaging configuration of the camera 31 of the robotic visualization system 30. In FIG. 3B, the camera 31 once again is a stereo camera comprising a first camera 34 and a second camera 35. Each of the cameras 34, 35 is depicted in a first pose with a first imaging configuration and in a second pose with a second imaging configuration, with a vertical distance between field of view 10, 11, 12 and cameras 34, 35 being shorter in the second pose than in the first pose. The optical axis 15 and respective rays from the camera 34, 35 to each corner of the visual field 10, 11, 12 are depicted in both imaging configurations for each of the cameras 34, 35. It is evident from FIG. 3B that for each camera 34, 35 the first pose corresponds to a first imaging configuration and the second pose corresponds to a second imaging configuration, with the respective imaging configuration being able to be characterized by the focal length 13, zoom level 14, and optical axis 15 of the camera 34, 35. Consequently, a plurality of combinations of possible poses and possible imaging configurations exist for the stereo camera 31 for each desired field of view 10, 11, 12. In this case, the possible imaging configurations are limited by the optical properties of the camera 31 and possible poses of the camera 31 are limited by the degrees of freedom of the robotic arm 32. In the method according to the invention, the possible poses are moreover limited by the requirement of a collision-free movement path from the current pose 20, as a result of which a further limitation of the possible imaging configuration of the camera 31 also arises.

In the operation of the RVS 30 according to an implementation of the method according to the invention, as depicted in FIG. 2, the adapted target pose 22 of the RVS 30, in particular of the camera 31, is shifted along the optical axis of the camera 31 or along a normal direction of the target field of view 11 vis-à-vis the target pose 21. In order to capture the same target field of view 11 as in the target pose 21 in the adapted target pose 22, it is consequently necessary to adapt the imaging configuration of the camera 31, in particular its focal length 13 and zoom level 14, as is evident from FIGS. 3A and 3B.

Figure 4:
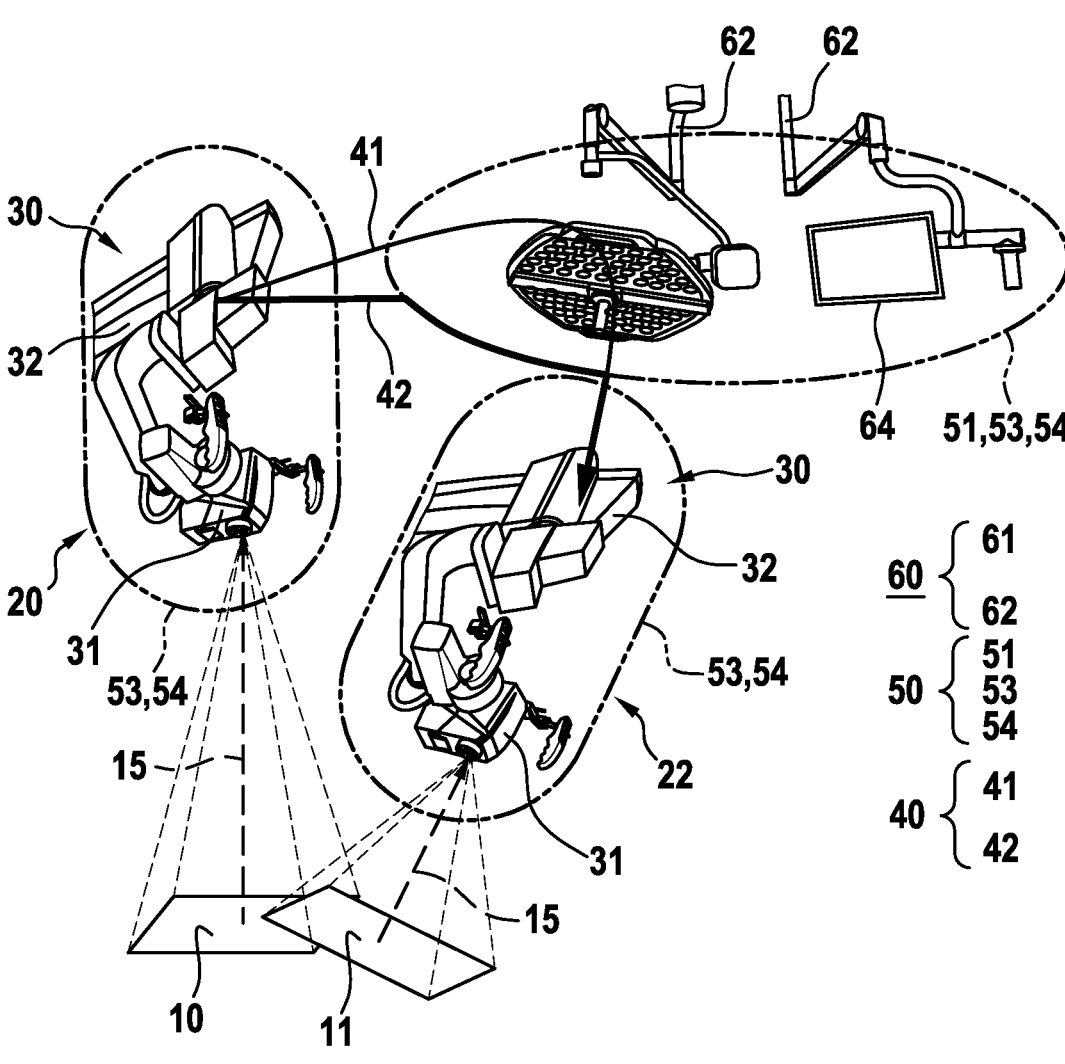
FIG. 4 shows a representation of an operation of the robotic visualization system according to an implementation of the method according to the invention.

FIG. 4 shows a further representation of an exemplary operation of the RVS 30 according to an implementation of the method according to the invention. In the representation of FIG. 4, the RVS 30 and objects in the surround 60 are approximated by simple (primitive) geometric shapes 54 in a 3-D model 50 of the surround 60. In particular, the RVS 30, as a dynamic object 53, is approximated by an ellipsoid 53. A mount 62 for a lamp and a screen 64, as a further dynamic object 54, is also approximated by an ellipsoid 53 and moreover defined as a region 51 that has been blocked for the RVS 30.

Using the 3-D model 50 of the surround 60, it is ascertained that there will be a collision, that is to say an overlap, of the ellipsoids 54 of RVS 30 and mount 62 along a movement path 41 from the current pose 20 of the RVS 30 to a target pose (not depicted) for capturing a target field of view 11. Consequently, a collision probability which exceeds a threshold value, for example zero, has been ascertained for the movement path 41. Accordingly, the 3-D model 50 of the surround 60, in particular of the approximated spatial shapes of RVS 30 and mount 62, is used again to ascertain an alternative movement path 42 to an adapted target pose 22, along which path there is no collision between the RVS 30 and the mount 62. In this case, an image of the target field of view 11 is likewise able to be captured from the adapted target pose 22, albeit using a (second) imaging configuration that differs from a current imaging configuration.

As is evident from FIG. 4, the adapted target pose 22 has merely been shifted from the original target pose (not depicted) along the optical axis 15 of the camera 31 in the target pose. In order to nevertheless capture an image of the desired target field of view 11, the second imaging configuration has a different focal length and zoom level in comparison with the current (first) imaging configuration. With the second imaging configuration, an image of the desired target field of view 11 is able to be captured in the adapted target pose 22.

Figure 5:
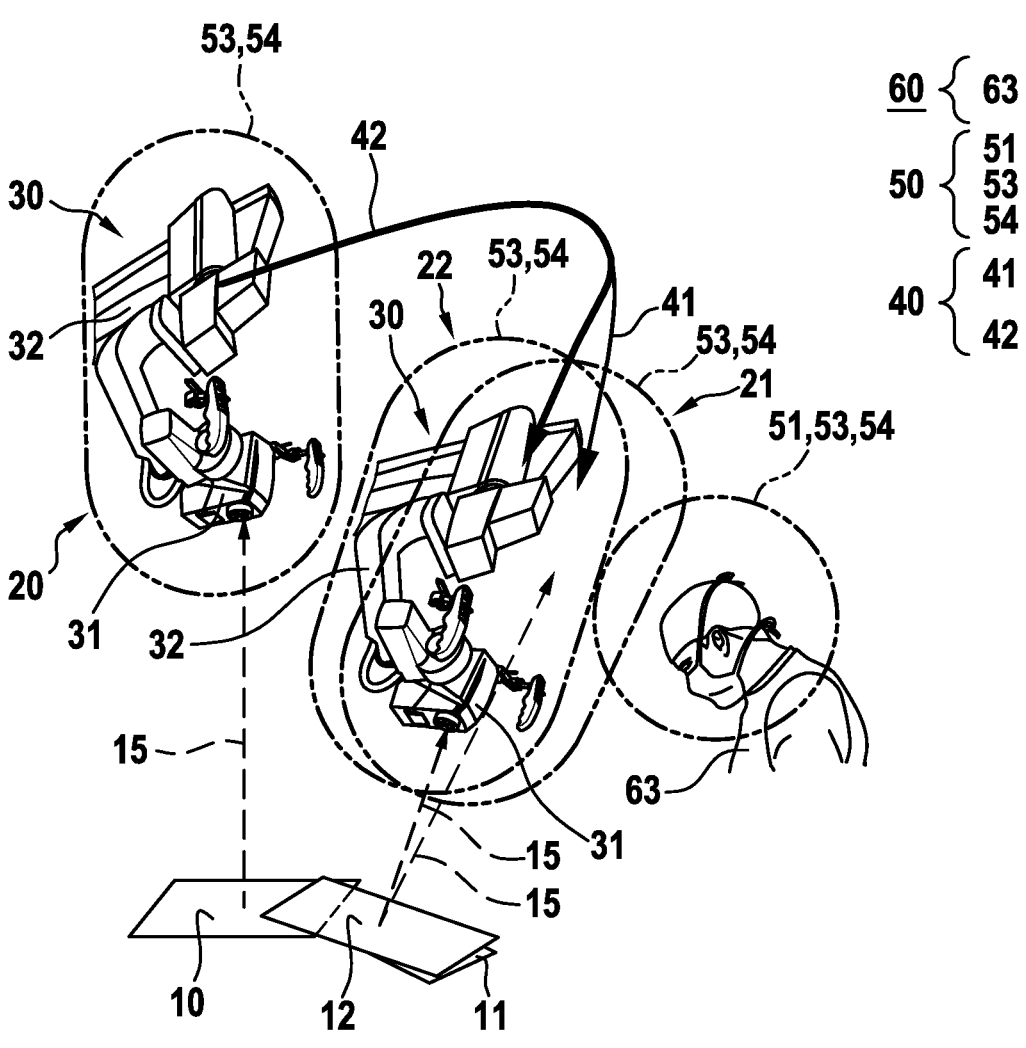
FIG. 5 shows a representation of an operation of the robotic visualization system according to an implementation of the method according to the invention.

FIG. 5 shows a representation of an exemplary operation of the RVS 30 according to a further implementation of the method according to the invention. In the representation of FIG. 5, the RVS 30 and objects in the surround 60 are also approximated by simple (primitive) geometric shapes 54 in a 3-D model 50 of the surround 60. In addition to the mount 62, a user 63, as a further dynamic object 54, is now also approximated by an ellipsoid 53 and moreover defined as a region 51 that has been blocked for the RVS 30.

Using the 3-D model 50 of the surround 60, it is ascertained that there will be a collision, that is to say an overlap, of the ellipsoids 54 of RVS 30 and user 63 along a movement path 41 from the current pose 20 of the RVS 30 to a target pose 21 for capturing a target field of view 11. Since the region 53, 54 approximating the user 63 is defined as a region 51 blocked for the RVS 30, a collision probability which exceeds a threshold value is ascertained on account of the overlap. Therefore, the 3-D model 50 of the surround 60, in particular of the approximated spatial shapes of RVS 30 and user 63, is used in turn to ascertain an alternative movement path 42 to an adapted target pose 22, along which path there is no collision between RVS 30 and user 63. As is evident from FIG. 5, the optical axis 15 of the adapted target pose 22 has been pivoted (tilted) vis-à-vis the optical axis of the original target pose 21. Beyond this, there is no shift of the adapted target pose 22 vis-à-vis the original target pose 21, for example no shift along the optical axis 15 of the camera 31 in the target pose 21. An identical image of the target field of view 11 is not able to be captured from the adapted target pose 22 on account of the pivoting of the optical axis 15.

However, an image of an adapted field of view 12, which has a very high degree of similarity with the target field of view 11, is able to be captured from the adapted target pose 22. In particular, the adapted field of view has an overlap with the target field of view 11, preferably an overlap of at least 80% of the areas of the fields of view 11, 12, further preferably an overlap of at least 90% of the areas of the fields of view 11, 12, and particularly preferably an overlap of at least 95% of the areas of the field of view 11, 12. Moreover, an imaged region of the adapted field of view 12 is identical to the imaged region of the target field of view 11. Consequently, the image content of an image of the adapted field of view 12 is largely identical to the image content of an image of the target field of view 11 and, in relation to the latter, merely has perspective distortions and/or shadowing of image details.

Figures 6, 7:
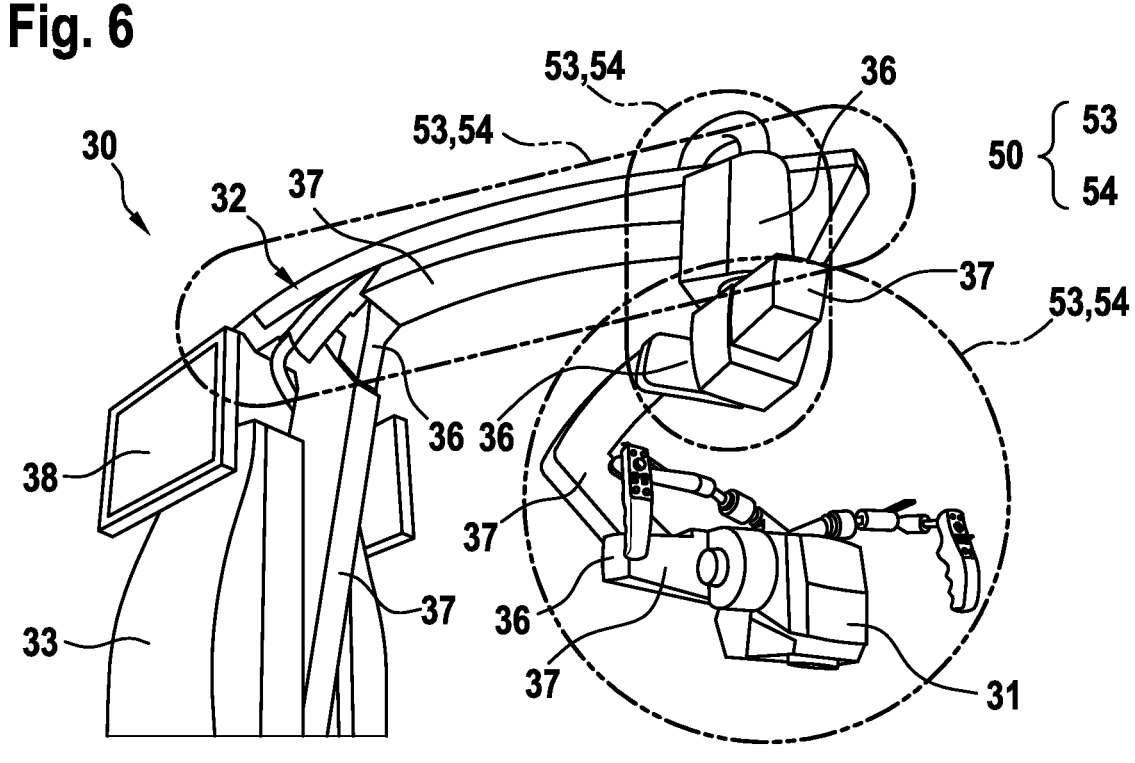
FIG. 6 shows a schematic representation of a robotic visualization system according to the invention in accordance with an embodiment.
FIG. 7 shows a schematic representation of a robotic visualization system according to the invention in accordance with a further embodiment.

FIG. 6 shows a schematic representation of a robotic visualization system 30 according to the invention in accordance with an embodiment of same. The RVS 30 comprises a camera 31, which is fastened to a robotic arm 32. The robotic arm 32 comprises a multiplicity of arm sections 37, which are interconnected via joints 36 in order to allow translational and/or rotational relative movements of the arm sections 37. The robotic arm 32 further comprises actuators in order to enable these relative movements, and hence a positioning of the camera 31. Moreover, the RVS 30 comprises a housing with a control unit 33 arranged therein and with a screen 38 arranged thereon. The control unit 33 is designed to control the robotic arm 32 and the camera 31, to the effect of positioning the camera 31 and using the latter to capture images. The images are processed by the control unit 33 and depicted on the screen 38.

As depicted in FIG. 6, the geometry of the RVS 30 is approximated by the combination of the three primitive 3-D shapes in a 3-D model 50 of the RVS 30. In particular, the robotic arm 32 is modeled by the combination of two ellipsoids 53 as a dynamic objects 54 and the camera 31 is modeled by a sphere 53 as dynamic object 54. On the basis of these primitive shapes 53, which have been connected to one another so as to allow relative motion, it is possible to create a kinematic model of the RVS 30, which is able to be integrated into the 3-D model 50 of the surround 60. Consequently, a movement path of the RVS 30 in the form of a channel of movement is able to be ascertained in the 3-D model 50, said channel of movement containing all adopted positions of the RVS 30 which are adopted when positioning the camera 31 from a first to a second position.

In this case, the 3-D model 50 of the surround 60 is based on static objects 52 modeled on the basis of user inputs or sensor data. These static objects 52, for example a wall 61 (cf. FIG. 1), are for example approximated by simple geometric shapes in the 3-D model 50, for example by a plane 54 (cf. FIG. 1). In the same way, ceilings and floors, and fixed furnishings can be approximated in the 3-D model 50. To this end, the fixed installation at a site of operation of the RVS 30 may also be detected once in sensor-assisted fashion. In order moreover to also take account of dynamic objects 53 in the surround 60 of the RVS 30 in the 3-D model 50 of the surround 60, the RVS 30 preferably comprises a plurality of sensors 39 for 3-D surround acquisition. These sensors preferably are a stereo camera, time-of-flight, TOF, camera systems, lidar systems and/or systems for structured light scanning. This is depicted in exemplary fashion in the schematic representation of an RVS 30 in FIG. 7.

Figure 8:
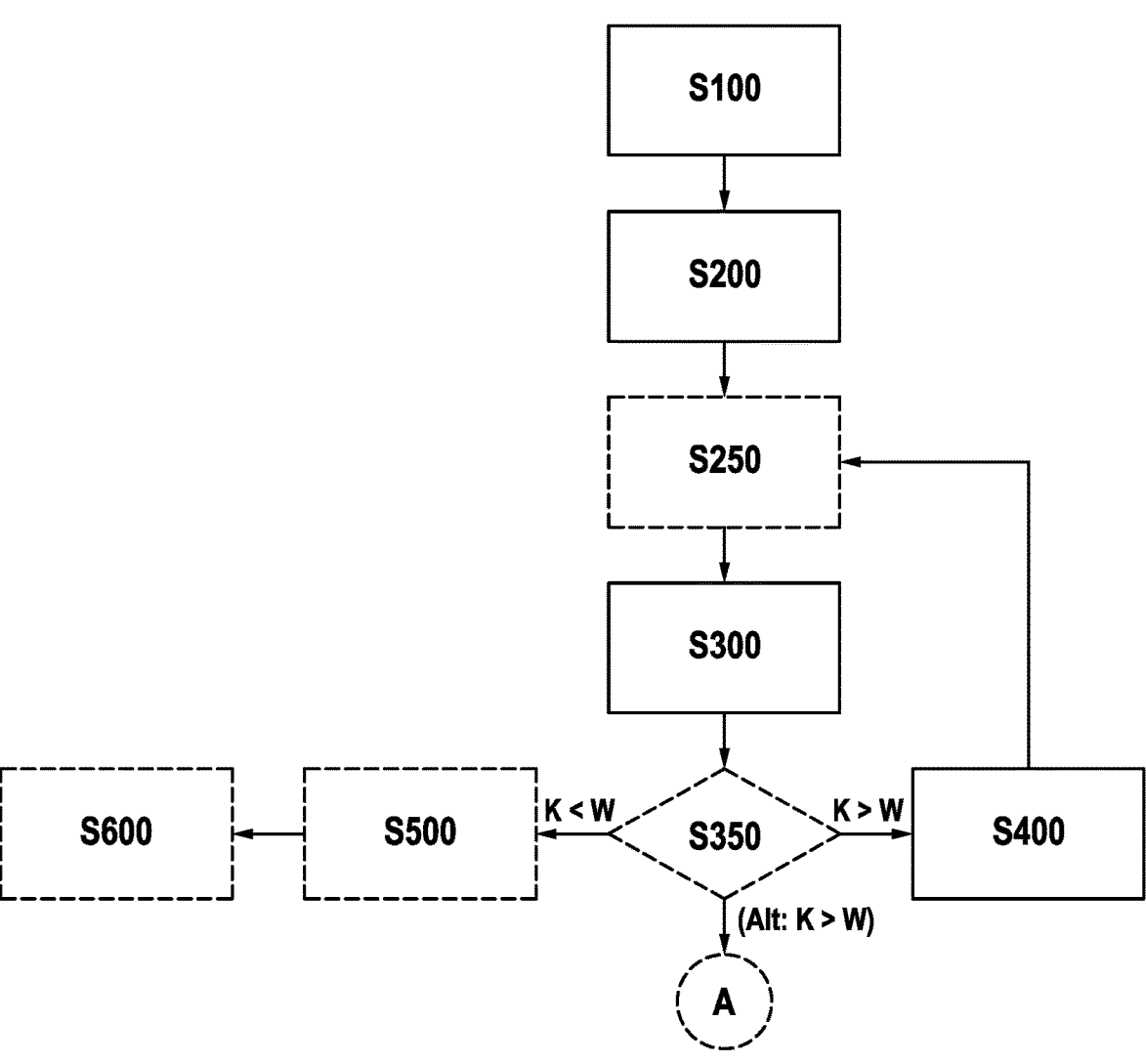
FIG. 8 shows a schematic flowchart of an implementation of the method according to the invention.

FIG. 8 shows a schematic flowchart of an implementation of the method according to the invention for operating a robotic visualization system 30 comprising a camera 31 that is fastened to a robotic arm 32 and hence positionable.

In a first step S100 of the method according to the invention, a target field of view 11 to be visualized by means of the camera 31 of the RVS 30 is ascertained S100. By way of example, this is implemented by capturing the viewing direction of a user or an alternative input.

In a second step S200, a target pose 21 of the RVS 30 for capturing an image of the target field of view 11 with a first imaging configuration of the camera 31 is ascertained. In this case, the first imaging configuration preferably is the current imaging configuration of the RVS 30. Consequently, only a positioning of the camera 31 would be necessary in order to image the target field of view 11. In this case, the target pose 21 is preferably ascertained by means of a kinematic model of the RVS 30, which for example is integrated into a 3-D surround model 50.

A 3-D model 50 of the surround 60 of the RVS 30 is created or updated in step S250. The 3-D model 50 of the surround 60 contains static objects 52 modeled as primitive 3-D shapes. By way of example, these parts of the 3-D model 50 are loaded from a memory. Additionally, the 3-D model 50 contains dynamic objects 53 modeled as primitive 3-D shapes. By way of example, these are modeled on the basis of regularly acquired sensor data from sensors for 3-D surround acquisition, which are fastened to the RVS 30. The 3-D model 50 of the surround 60 further contains an integrated kinematic 3-D model 50 of the RVS 30 with primitive shapes 54.

A collision probability K along a movement path 40 of the RVS 30 from a current pose 20 of the RVS 30 to the ascertained target pose 21 is ascertained in a further step S300 on the basis of the current 3-D model 50 of the surround 60. In particular, it is ascertained whether, during a movement of the RVS 30 from a current pose 20 of the RVS 30 to the ascertained target pose 21, there is an overlap between one of the primitive shapes 54 used to approximate the RVS 30 and one of the primitive shapes 54 used to approximate the surround 60. However, other factors may also be considered in order to ascertain the collision probability K, for example the degree of overlap or the like during the extrapolation of dynamic objects or the probability of the extrapolated movement and during the approximation of complex geometries by primitive shapes.

A check as to whether the ascertained collision probability K exceeds a predetermined threshold value W is carried out in a step S350. Should this not be the case, that is to say if the ascertained collision probability K is less than the threshold value W, the camera is positioned in the target pose
21 in a step S500 and an image of the target field of view 11
is captured with the camera 31 in the target pose 21 and in
a first imaging configuration in step S600. However, if the
ascertained collision probability K is greater than the thresh-
old value W, that is to say if a collision of the RVS 30 with
an object or subject in the surround 60 is probable, then an
adapted target pose 22 of the RVS 30 for capturing an image
corresponding to the target field of view 11 with a second
imaging configuration of the camera 31 is ascertained, to be
precise using the 3-D model 50 of the surround again, in a
step S400.

At least if the collision probability K was not already
taken into account directly during the ascertainment of the
adapted target pose 22, steps S300 and S350 are repeated
with the adapted target pose 22 replacing the target pose 21.
In this case, the 3-D model 50 of the surround 60 is initially
updated in step S250 on the basis of current sensor infor-
mation. Even if the collision probability K was already
directly taken into account when ascertaining the adapted
target pose 22, steps S300 and S 350 may be carried out as
an additional check for the adapted target pose 22 as well. If
the collision probability K is ascertained as being smaller
than the threshold value W for the adapted target pose 22, the
camera 31 is positioned in the adapted target pose 22 in step
S500 and an image corresponding to the target field of view
11 is captured in step S600 with the camera 31 in the adapted
target pose 22 and with the second imaging configuration.

Figure 9:
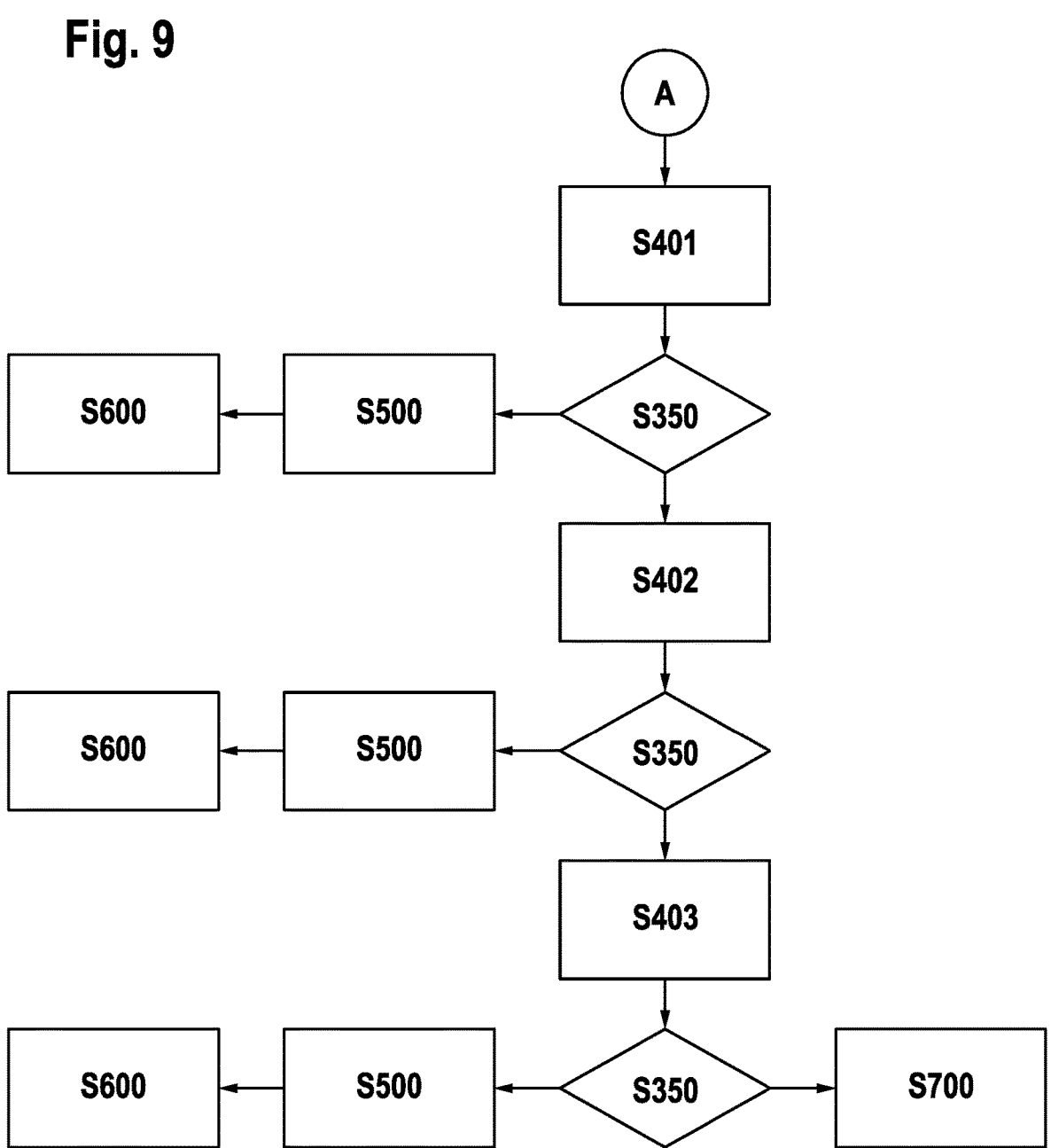
FIG. 9 shows a schematic flowchart of a further implementation of the method according to the invention.

FIG. 9 shows a schematic flowchart of a further imple-
mentation of the method according to the invention. In this
case, FIG. 9 represents a preferred implementation of the
method according to the invention, but is depicted as an
alternative implementation (Alt) for the case K>W in FIG.
8 for reasons of conciseness. Consequently, the steps
depicted in FIG. 9 are preceded by steps S100, S200, S300
depicted in FIG. 8, optionally also by steps S250 and S350
depicted as preferred in FIG. 8.

As depicted in FIG. 9, step S400 of ascertaining the
adapted target pose 22 of the RVS 30 includes a plurality of
successively and conditionally implemented steps.

In a first step S401, an attempt is made to ascertain a
collision-free movement path 42 from the current pose 20 of
the RVS to an adapted target pose 22, which target pose is
shifted from the target pose 21 ascertained in step S200 in
the normal direction of the target field of view 11 and/or
along the optical axis 15 of the camera 31. If such an adapted
target pose 22 can be ascertained, the camera 31 is posi-
tioned in the adapted target pose 22 in step S500 and an
image of the target field of view 11 is captured in step S600
with the camera 31 in the adapted target pose 22 and with the
second imaging configuration.

If such an adapted target pose 22 cannot be ascertained, an
attempt is made to ascertain a collision-free movement path
42 from the current pose 20 of the RVS 30 to an alternative
adapted target pose 22 in a second step S402, which target
pose has a pivoted optical axis 15 of the camera 31 vis-à-vis
the target pose 21 ascertained in step S200. If such an
adapted target pose 22 can be ascertained, the camera 31 is
positioned in the adapted target pose 22 in step S500 and an
image corresponding to the target field of view 11 is cap-
tured in step S600 with the camera 31 in the adapted target
pose 22 and with the second imaging configuration.

If such an adapted target pose 22 cannot be ascertained, an
attempt is made to ascertain a collision-free movement path
42 from the current pose 20 of the RVS 30 to an alternative
adapted target pose 22 in a third step S403, which target pose
has a laterally shifted optical axis 15 of the camera 31 vis-à-vis the target pose 21. If such an adapted target pose 22
can be ascertained, the camera 31 is positioned in the
adapted target pose 22 in step S500 and an image corre-
sponding to the target field of view 11 is captured in step
S600 with the camera 31 in the adapted target pose 22 and
with the second imaging configuration. If such an adapted
target pose 22 cannot be ascertained, the method ends in step
S700 with a user notification that an image corresponding to
the target field of view 11 is not able to be captured on
account of the risk of a collision.

Figure 10:
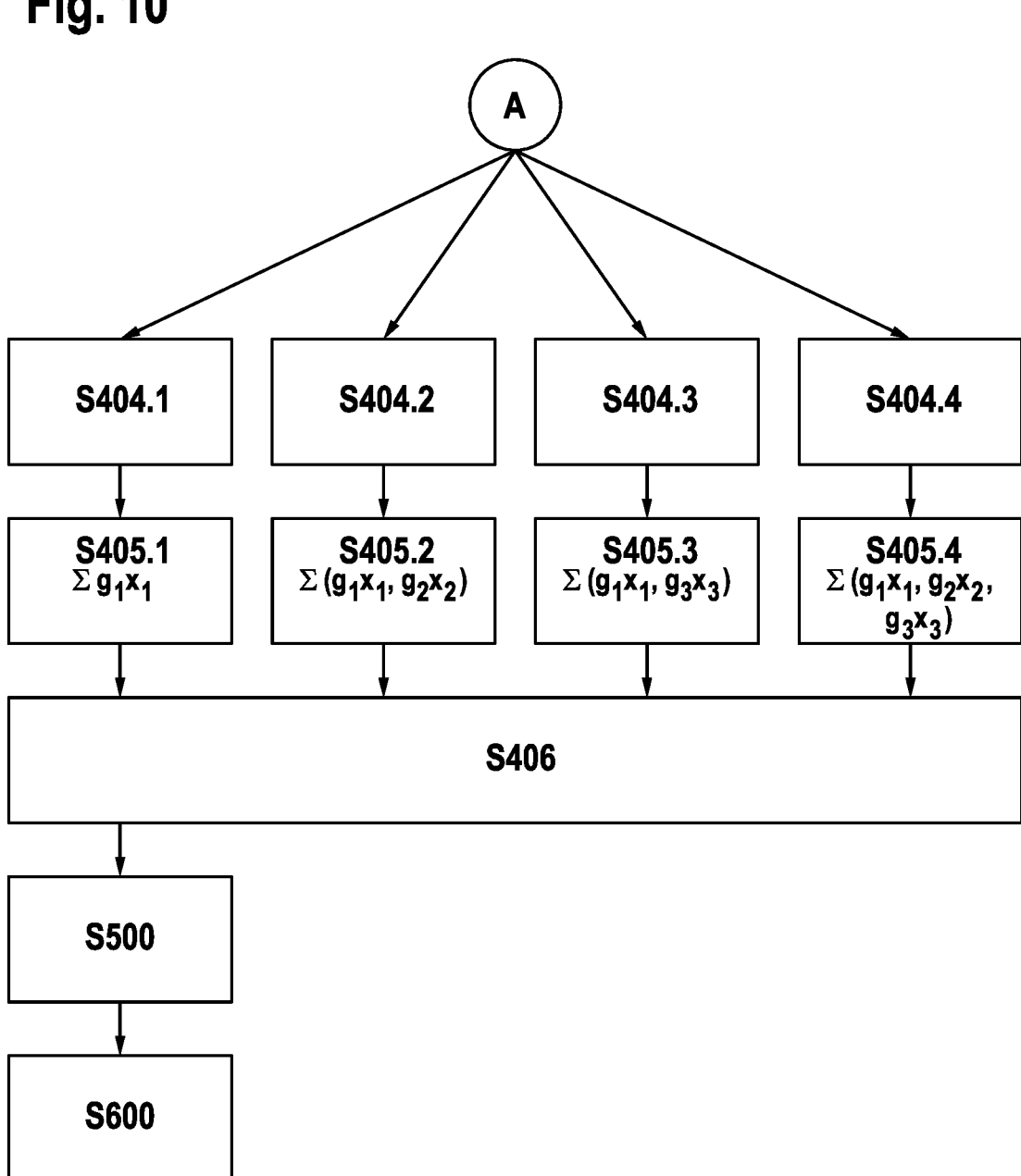
FIG. 10 shows a schematic flowchart of a further implementation of the method according to the invention.

FIG. 10 shows a schematic flowchart of a further imple-
mentation of the method according to the invention. In this
case, FIG. 10 represents a preferred implementation of the
method according to the invention, but is depicted as an
alternative implementation (Alt) for the case K>W in FIG.
8 for reasons of conciseness. Consequently, the steps
depicted in FIG. 10 are preceded by steps S100, S200, S300
depicted in FIG. 8, optionally also by steps S250 and S350
depicted as preferred in FIG. 8.

According to FIG. 10, step S400 of ascertaining the
adapted target pose 22 of the RVS 30 includes ascertaining
S404 a plurality of collision-free movement trajectories 42
from the current pose 20 to a plurality of possible adapted
target poses 22. In FIG. 10, this is depicted by the ascer-
tainment S404.1 of a first collision-free movement path 42
from the current pose to a first possible target pose, the
ascertainment S404.2 of a second collision-free movement
path 42 from the current pose to a second possible target
pose, the ascertainment S404.3 of a third collision-free
movement path 42 from the current pose to a third possible
target pose, and the ascertainment S404.4 of a fourth colli-
sion-free movement path 42 from the current pose to a fourth
possible target pose.

For each of the possible adapted target poses 22, a value
of a target function characterizing the adapted target pose 22
is subsequently ascertained in step S405 on the basis of
features $x_i$ of said adapted target pose 22. In this case, the
characterizing value is ascertained on the basis of a weighted
sum $\Sigma g_i x_i$ of features $x_i$ of the adapted target pose 22. In this
case, a first weight $g_1$ corresponds to the shift $x_1$ of the
camera 31 vis-à-vis the target pose 21 along the optical axis
15 of the camera 31 (or in the normal direction of the target
field of view), a second weight $g_2$ corresponds to a pivoting
$x_2$ of the optical axis 15 of the camera 31 vis-à-vis the target
pose 21, and a third weight $g_3$ corresponds to a shift $x_3$ of the
optical axis 15 of the camera 31 vis-à-vis the target pose 21.
The second weight $g_2$ is greater than the first weight $g_1$ and
less than the third weight $g_3$.

What is considered in step S405 in FIG. 10 is that the
adapted target pose 22 to be reached collision-free according
to step S404.1 is reachable by a shift along the optical axis
of the camera 31, the adapted target pose 22 to be reached
collision-free according to step S404.2 is reachable by a shift
along the optical axis of the camera 31 in combination with
a pivot of the optical axis, the adapted target pose 22 to be
reached collision-free according to step S404.3 is reachable
by a shift along the optical axis of the camera 31 in
combination with a lateral shift of the optical axis, and the
adapted target pose 22 to be reached collision-free according
to step S404.2 is reachable by a shift along the optical axis
of the camera 31 in combination with a pivot and a lateral
shift of the optical axis of the camera 31. Consequently, a
smallest weighted mean arises in step S405.1 and a largest
weighted mean arises in step S405.4. Between these are the
weighted means ascertained in steps S405.2 and S405.3,
with the weighted mean ascertained in step S405.2 being
smaller than the weighted mean ascertained in step S505.3.

In a step S406, the adapted target pose 22 to be reached collision-free according to step S404.1 is finally selected since the latter has a local or global minimum of the target function as characterizing value. Finally, the camera 31 is positioned in the adapted target pose 22 in step S500 and an image of the target field of view 11 is captured in step S600 with the camera 31 situated there and the second imaging configuration.

LIST OF REFERENCE SIGNS

10 Current field of view
11 Target field of view
12 Adapted field of view
13 Focal length
14 Zoom level
15 Optical axis
16 Operating region
20 Current pose
21 Target pose
22 Adapted target pose
30 Robotic visualization system
31 Camera
32 Robotic arm
33 Control unit
34 First camera of a stereo camera
35 Second camera of a stereo camera
36 Joint
37 Arm section
38 Screen
39 Sensors for 3-D surround acquisition
40 Movement path
41 Movement path with collision
42 Movement path without collision
50 3-D model of the surround
51 Blocked region
52 Static object
53 Dynamic object
54 Simple 3-D shape
60 Surround
61 Wall
62 Mount for luminaire/screen
63 Person
64 Further screen

The invention claimed is:

1. A method for operating a robotic visualization system comprising an imaging optical unit, a control unit, and a robotic arm for positioning the imaging optical unit within a surround, the method including the method steps of:
   ascertaining, by the control unit, a target field of view to be visualized by means of the imaging optical unit, the imaging optical unit being attached to the robotic arm;
   ascertaining, by the control unit, a target pose of the robotic visualization system for capturing an image of the target field of view with a first imaging configuration of the imaging optical unit;
   ascertaining, by the control unit, a collision probability along a movement path of the robotic visualization system from a current pose of the robotic visualization system to the ascertained target pose using a 3-D model of the surround;
   ascertaining, by the control unit, an adapted target pose of the robotic visualization system for capturing an image corresponding to the target field of view with a second imaging configuration of the imaging optical unit using the 3-D model of the surround, should the ascertained collision probability exceed a predetermined threshold value; and
   causing, by the control unit, execution of a positioning of the imaging optical unit in the adapted target pose using the robotic arm.

2. The method as claimed in claim 1, wherein the second imaging configuration has an adapted focal length and/or an adapted zoom level in relation to the first imaging configuration.

3. The method as claimed in claim 1, wherein the adapted target pose has been shifted vis-à-vis the target pose in the normal direction of the target field of view and/or along the optical axis of the imaging optical unit in the target pose.

4. The method as claimed in claim 1, further including the method step of capturing, with the second imaging configuration, the image of the target field of view corresponding to the target field of view.

5. The method as claimed in claim 1, wherein the ascertainment of the adapted target pose of the robotic visualization system comprises the following steps:
   (a) ascertaining a collision-free movement path to an adapted target pose which has been shifted from the target pose in the normal direction of the target field of view and/or along the optical axis of the imaging optical unit,
   (b) ascertaining a collision-free movement path to an adapted target pose with an optical axis of the imaging optical unit that has been pivoted vis-à-vis the target pose, provided no movement path is ascertainable in step (a), and
   (c) ascertaining a collision-free movement path to an adapted target pose with an optical axis of the imaging optical unit that has been shifted vis-à-vis the target pose, provided no movement path is ascertainable in step (b).

6. The method as claimed in claim 5, wherein the image corresponding to the target field of view is captured from an adapted field of view that overlaps with the target field of view, provided no movement path is ascertainable in step (a).

7. The method as claimed in claim 1, wherein the ascertainment of the adapted target pose of the robotic visualization system comprises the following steps:
   ascertaining collision-free movement trajectories from the current pose to a plurality of possible adapted target poses;
   ascertaining, for each of the possible adapted target poses, a value of a target function characterizing the adapted target pose on the basis of features xi of said adapted target pose; and
   selecting one of the possible adapted target poses with a local or global extremum of the target function as characterizing value.

8. The method as claimed in claim 7, wherein the characterizing value is ascertained on the basis of a weighted sum $\Sigma g_i x_i$ of features $x_i$ of the adapted target pose,
   with a first weight $g_1$ corresponding to a shift $x_1$ of the imaging optical unit vis-à-vis the target pose in the normal direction of the target field of view and/or along the optical axis of the imaging optical unit,
   with a second weight $g_2$ corresponding to a pivoting $x_2$ of the optical axis of the imaging optical unit vis-à-vis the target pose, and
   with a third weight $g_3$ corresponding to a shift $x_3$ of the optical axis of the imaging optical unit vis-à-vis the target pose.

9. The method as claimed in claim 8, wherein the second weight $g_2$ is greater than the first weight $g_1$ and less than the third weight $g_3$, and the characterizing value of the selected adapted target pose represents a minimum of the target function.

10. The method as claimed in claim 7, wherein features $x_i$ of the adapted target pose comprise an adjustment of the imaging configuration of the imaging optical unit, a height of the imaging optical unit and/or of the robotic visualization system, user-defined boundary conditions, a displacement time and/or a displacement path from the current pose to the adapted target pose, and/or a distance of imaging optical unit and target field of view.

11. The method as claimed in claim 1, wherein the 3-D model of the surround defines at least one region that is blocked for the robotic visualization system.

12. The method as claimed in claim 1, wherein the 3-D model of the surround represents static objects and/or dynamic objects within the surround and/or the robotic visualization system as simple 3-D shapes.

13. The method as claimed in claim 1, wherein the 3-D model of the surround is based on a sensor-assisted detection of the surround.

14. A robotic visualization system for use in medical operations, the robotic visualization system comprising:
    an imaging optical unit having a zoom lens;
    a robotic arm configured to position the imaging optical unit, and a control unit configured to control the imaging optical unit and the robotic arm to carry out the steps of:
ascertaining a target field of view to be visualized by means of the imaging optical unit, the imaging optical unit being attached to the robotic arm;
ascertaining a target pose of the robotic visualization system for capturing an image of the target field of view with a first imaging configuration of the imaging optical unit;
ascertaining a collision probability along a movement path of the robotic visualization system from a current pose of the robotic visualization system to the ascertained target pose using a 3-D model of the surround;
ascertaining an adapted target pose of the robotic visualization system for capturing an image corresponding to the target field of view with a second imaging configuration of the imaging optical unit using the 3-D model of the surround, should the ascertained collision probability exceed a predetermined threshold value; and
causing execution of a positioning of the imaging optical unit in the adapted target pose using the robotic arm.

15. The robotic visualization system as claimed in claim 14, further comprising a stereo camera having a zoom lens as imaging optical unit and/or sensors configured for the three-dimensional detection of the surround.

* * * * *